United States Patent
Marzi et al.

[11] Patent Number: 5,298,621
[45] Date of Patent: Mar. 29, 1994

[54] OLIGOPEPTIDE DERIVATIVES OF IPOXANTINE ENDOWED WITH IMMUNOMODULATING ACTIVITY AND PHARMACEUTICAL COMPOSITIONS CONTAINING SAME

[75] Inventors: Mauro Marzi; Patrizia Minetti, both of Rome; Piero Foresta, Pomezia; Maria O. Tinti, Rome, all of Italy

[73] Assignee: Sigma-Tau Industrie Farmaceutiche Riunite S.P.A., Rome, Italy

[21] Appl. No.: 723,418

[22] Filed: Jun. 28, 1991

[30] Foreign Application Priority Data

Jun. 28, 1990 [IT] Italy ................ 48102 A/90

[51] Int. Cl.$^5$ ............................. C07K 5/06
[52] U.S. Cl. ........................ 544/265; 544/276; 544/275; 530/330; 530/331
[58] Field of Search ........ 514/262, 885, 17, 18, 514/19; 544/276, 277, 265; 530/330, 331

[56] References Cited

U.S. PATENT DOCUMENTS 4,567,182 1/1986 Ferraris ..................... 514/262

FOREIGN PATENT DOCUMENTS

WO 89/05818 6/1989 PCT Int'l Appl.
8905818 6/1989 World Int. Prop. O.

OTHER PUBLICATIONS

Il Farmaco, vol. 45, No. 1, 1990, pp. 39–47, R. Stradi, et al., "Synthetic Biological Response Modifiers; Part 1. Synthesis and Immunomodulatory Properties of Some N2-(w(Hypoxanthin-9-YL)Alkoxycarbonyl-L-Arginines".

Primary Examiner—Lester L. Lee
Attorney, Agent, or Firm—Oblon, Spivak, McClelland, Maier & Neustadt

[57] ABSTRACT

Ipoxantine derivatives of general formula (I):

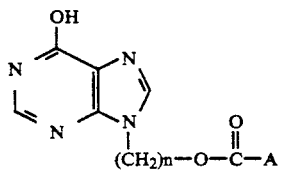

both as racemate and chiral forms and the salts thereof with pharmacologically acceptable cations, wherein n is an integer comprised between 2 and 6, and A is the residue of a dipeptide, tripeptide, tetrapeptide and pentapeptide selected, respectively, from the groups consisting of:

(a) glycyl-aspartate, alanyl-glycine, glycyl-glycine, aspartyl-arginine, leucyl-arginine;

(b) arginyl-lysyl-aspartate, aspartyl-lysyl-arginine, lysyl-prolyl-arginine, prolyl-prolyl-arginine, lysyl-histidyl-glycinamide, prolyl-phenilalanyl-arginine, phenylalanyl-prolyl-arginine;

(c) arginyl-lysyl-aspartyl-valine (SEQ ID NO: 1), valyl-aspartyl-lysyl-arginine (SEQ ID NO: 2), threonylvalyl-leucyl-histidyne (SEQ ID NO: 3); and (d) arginyl-lysyl-aspartyl-valyl-tyrosine (SEQ ID NO: 4);

are endowed with immunomodulating activity and can be formulated in orally or parenterally administrable pharmaceutical compositions.

2 Claims, No Drawings

OLIGOPEPTIDE DERIVATIVES OF IPOXANTINE ENDOWED WITH IMMUNOMODULATING ACTIVITY AND PHARMACEUTICAL COMPOSITIONS CONTAINING SAME

The present invention relates to ipoxantine oligopeptide derivatives of general formula (I):

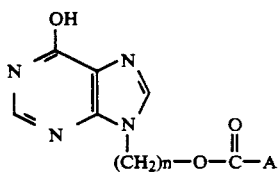

both as racemate and chiral forms and the salts thereof with pharmacologically acceptable cations, wherein n is an integer comprised between 2 and 6, preferably 5, and A is the residue of a dipeptide, tripeptide, tetrapeptide and pentapeptide selected, respectively, from the groups consisting of:

(a) glycyl-aspartate, alanyl-glycine, glycyl-glycine, aspartyl-arginine, leucyl-arginine;

(b) arginyl-lysyl-aspartate, aspartyl-lysyl-arginine, lysyl-prolyl-arginine, prolyl-prolyl-arginine, lysyl-histidyl-glycinamide, prolyl-phenylalanyl-arginine, phenylalanyl-prolyl-arginine;

(c) arginyl-lysyl-aspartyl-valine (SEQ ID NO: 1), valyl-aspartyl-lysyl-arginine (SEQ ID NO: 2), threonylvalyl-leucyl-histidyne (SEQ ID NO: 3); and (d) arginyl-lysyl-aspartyl-valyl-tyrosine (SEQ ID NO: 4).

These oligopeptides are endowed with immunomodulating activity and can be formulated in orally or parenterally administrable pharmaceutical compositions.

The known compound that, to the applicant's knowledge, is the closest one to the compounds of the invention and whose pharmacological data supporting its immunomodulating activity are described in the literature is N-5-(ipoxantin-9-yl) pentyloxycarbonyl arginine (see EP 0077460 and Il Farmaco, 45 (1), 39–47, 1990).

Other similar compounds, i.e. ipoxantine dipeptides and tripeptides wherein, however, the oligopeptide moiety is other than that of the present compounds, are named in PCT 89/05818. The physico-chemical characteristics of these compounds, however, are not disclosed, nor pharmacological data supporting their alleged immunomodulating activity are given. Therefore, having regard to this state of the art, the applicant considers the compound disclosed in EP 0077460 the reference compound and has found that the present compounds are more potent immunomodulating agents than the known compound.

The compounds of general formula (I) are prepared as shown in the following reaction scheme (for the sake of simplicity, n=5).

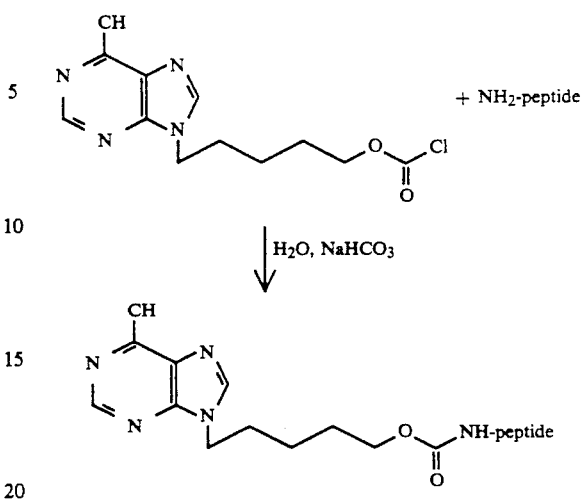

The condensation reaction between the peptide and the intermediate chlorocarbonate takes place in an alkaline aqueous environment, at temperatures comprised between 10° C. and 40° C., for 12–48 hours, reactants molar ratio 1:1–2:1. The raw reaction product is purified by chromatography on silica gel with eluants such as ethylacetate-methanol in varying ratios, or by ionic exchange chromatography with acid and basic resins.

If the utilized peptide contains a further functional group, in the condensation reaction the suitably protected dipeptide is used and subsequently the protecting group is removed via techniques well known in peptide synthesis. For instance, if the protecting group is carbobenzoxy (hereinafter designated "Z"), its removal is achieved via catalytic hydrogenation in an acidic hydroalcoholic solution in the presence of 5% or 10% Pd/C hydrogenation catalyst, for 3–24 hours.

The following non-limiting examples illustrate the preparation of some compounds of the present invention.

EXAMPLE 1

Preparation of N-5-(ipoxantin-9-yl) pentyloxycarbonyl glycylglycine sodium salt (ST 742)

Glycylglycine (10 g; 0.076 moles) was dissolved in a solution of $NaHCO_3$ (19.15 g; 0.228 moles) in 300 mL $H_2O$. To the resulting solution 9-[5-(chlorocarbonyloxy)pentyl]ipoxantine hydrochloride (26.7 g; 0.083 moles) was added portionwise. The reaction mixture was kept under stirring at room temperature for 12 hours. The resulting mixture was then concentrated to dryness under vacuum. The residue was dissolved in methanol and chromatographed on silica gel eluting with ethylacetatemethanol (3:7). The fractions were pooled and concentrated, and the residue thus obtained was dissolved in $H_2O$ and lyophilized. 21 g of the title compound were obtained. Yield: 70%.

TLC AcOEt: MeOH 1:9 Rf=0.7

E.A. corresponds to $C_{15}H_{19}N_6NaO_6$

M.P. (product containing 6% $H_2O$) (soft. 79°–88° C.)=140° C.

NMR H'(300 MHz) $D_2O$ δ8,2 (1H,s,arom); 8,1 (1H,s,arom);

4,25(2H, t, C̲H₂—OC—); 4,05(2H, t, CH₂—N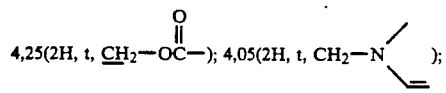);

3,9(2H, s, C̲—N—CH₂—CO);

3,81 (2H,s,NCH₂—CO); 1,9 (2H,m,CH₂—C—OC=O); 1,65 (2H,m,CH₂—C—N); 1,15 (2H,m,C—CH₂—C)

EXAMPLE 2

Preparation of N-5-(ipoxantin-9-yl) pentyloxycarbonyl glycyl L-aspartate disodium salt (ST 657/Na₂)

The compound was prepared as described in Example 1. Yield: 80%.
TLC MeOH Rf=0.3
EA corresponds to $C_{17}H_{20}N_6Na_2O_8$
MP (soft. 120° C.)=150° C.
$[\alpha]_D^{25} = +12.8$ (0.8% H₂O)
NMR H' (300 MHz) D₂O δ8,2 (1H,s,arom) 4,25 (2H,t,CH₂—OC=O);

4,05(2H, t, CH₂—N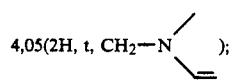);

3,9(3H, s+m, CH₂—C̲N, C̲H—COOMe);

2,8(2H, m, C̲H₂—COONa) 1,9(2H, m, CH₂—C—O);

1,7(2H, m, CH₂—C—N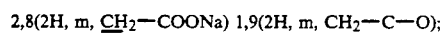); 1,4(2H, m, C—CH₂—C)

EXAMPLE 3

Preparation of N-5-(ipoxantin-9-yl) pentyloxycarbonyl L-alanyl-glycine sodium salt (ST 733)

The compound was prepared as described in Example 1. Yield: 70%.
TLC AcOEt: MeOH 4:6 Rf=0.6
EA corresponds to $C_{16}H_{21}N_6NaO_6$
MP (product containing 4% H₂O) (soft. 90° C.)=94° C.
$[\alpha]_D^{25} = -10.1°$ (1% H₂O)
NMR H' (300 MHz) D₂O δ8,2 (1H,s,arom); 8,1 (1H,s,arom);

4,25(2H, t, CH₂—OC̲); 4,1-4,0(3H, m, CH—C̲, CH₂—N ) | CH₃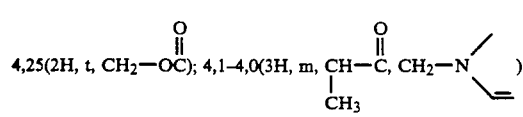

1,9(2H, m, CH₂—C—OC=O); 1,6(2H, m, CH₂—C—N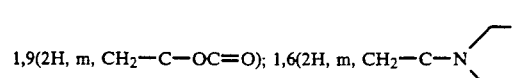

1,4-1,2(5H, m, C̲H₃, C—C̲H₂—C)

EXAMPLE 4

Preparation of N-5-(ipoxantin-9-yl) pentyloxycarbonyl L-(alpha) aspartyl L-arginine sodium salt (ST 754)

The compound was prepared as described in Example 1. Yield: 65%.
TLC AcOEt: MeOH 1:9 Rf=0.5
EA corresponds to $C_{21}H_{30}N_9NaO_8$
MP (product containing 6% H₂O) (soft. 70° C.)=86° C.
$[\alpha]_D^{25} = +7.8$ (1% H₂O)
NMR H' (300 MHz) H' D₂O δ8,2 (1H,s,arom); 8,1 (1H,s,arom);

4,42(1H, t, —C̲H—C—N); 4,2(3H, t, C̲H₂—OC, N—C̲H—COH);

4,05(2H, t, C̲H₂—N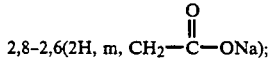); 3,1(2H, d, CH₂—N—C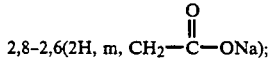);

2,8-2,6(2H, m, CH₂—C—ONa);

2-1,4(8H, m, CH₂—CH₂CH₂—CO, —CH₂—C—N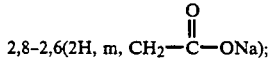);

1,4(2H, m, C—CH₂—C)

EXAMPLE 5

Preparation of N-5-(ipoxantin-9-yl) pentyloxycarbonyl L-alanyl-arginine ST 785)

The compound was prepared as described in Example 1. Yield: 56%.
TLC MeOH Rf=0.3
MP (product containing 5% H₂O) (soft. 170° C.)=188° C.
$[\alpha]_D^{25} = -9,4°$ (C=1% H₂O)
NMR H' (300 MHz) D₂O δ8,2 (1H,s,arom); 8,1 (1H,s,arom); 4,4-3,9 (6H,m,NC̲H—CON,N—C̲H—COO;

C̲H₂—N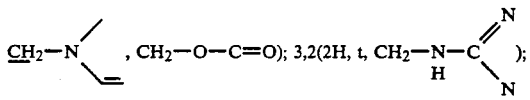, CH₂—O—C=O); 3,2(2H, t, CH₂—N—C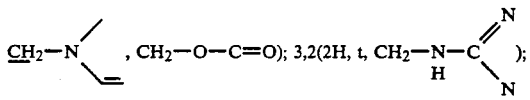);

2-1,5(6H, m, CH₂—CH₂, CH₂—C—O, CH₂—C—N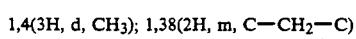);

1,4(3H, d, CH₃); 1,38(2H, m, C—CH₂—C)

EXAMPLE 6

Preparation of N-5-(ipoxantin-9-yl) pentyloxycarbonyl L-leucyl L-arginine (ST 786)

The compound was prepared as described in Example 1. Yield: 80%.
TLC MeOH Rf=0.28
EA=corresponds to $C_{23}H_{37}N_9O_6$
MP (product containing 8% H₂O) (soft. 170° C.)=188° C.

$[\alpha]_D^{25} = -11.8$ (1% $H_2O$)

NMR H' (300 MHz) $D_2O$ δ8,2 (1H,s,arom);

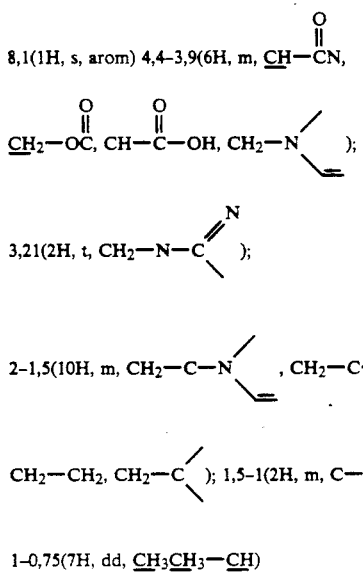

8,1(1H, s, arom) 4,4–3,9(6H, m, C̲H—CN, 3,21(2H, t, $CH_2$—N—C⟨$^N$ );

2–1,5(10H, m, $CH_2$—C—N⟨ , $CH_2$—C—OC=, $CH_2$—$CH_2$, $CH_2$—C⟨ ); 1,5–1(2H, m, C—$CH_2$—C);

1–0,75(7H, dd, C̲H₃C̲H₃—C̲H)

EXAMPLE 7

Preparation of N-5-(ipoxantin-9-yl) pentyloxycarbonyl L-arginyl L-lysyl L-aspartate (ST 848)

5.54 g (0.064 moles) of $NaHCO_3$ were dissolved in water and to the resulting solution, upon cooling, 6.71 g (0.01 moles) of protected tripeptide (Arg-Lys(Z)-Asp).$2CH_3COOH$ were added. To this mixture 3.52 g (0.011 moles) 9-(5-chlorocarbonyloxypentyl) ipoxantine hydrochloride were then added portionwise.

The resulting reaction mixture was kept under stirring overnight and, upon reaction termination, brought to dryness. The product thus obtained was purified in a silica gel column, eluting with AcOEt: MeOH 2:8.

6.2 g of an intermediate product were obtained that was catalytically hydrogenated with 10% Pd/C at the pressure of 3 atmospheres in a $H_2O$/MeOH/$CH_3COOH$ (50 mL/150 mL/30 mL) mixture. After 12 hours, the catalyst was filtered off and the filtrate brought to dryness at 40° C.

The product thus obtained was dissolved in water and the solution was lyophilized. 2.8 g of the title compound as an adduct with 2 molecules of $CH_3COOH$ were obtained.

Yield 34%

$[\alpha]_D = -14.2$ (c=1% $H_2O$)

The compound softens at 125°–145° C. and decarboxylates at 146° C.

EA corresponds to $C_{31}H_{49}N_{11}Na_2O_{13}$

HPLC: column μ Bondapack $C_{18}$; eluant 0.05M $KH_2PO_4$-$CH_3CN$ (90:10);

U.V. detector: λ=205 nm; Refraction Index; flow rate: 1 mL/min;

Retention time: 6.90 minutes

NMR (300 MHz) DMSO/$D_2O$ intermediate δ8.1 (2H,2s,2CH ipoxantine); δ7.4–7.2 (5H,m,arom) δ5.1 (2H,s,$CH_2$—O); δ4,4–3,8 (11H,m,3CH—N,$CH_2$—O,C-$H_2$—N,$CH_2$—NH—C,$CH_2$—N); δ3.3 (2H,m,C$\underline{H}_2$—COO); δ2-1 (16H,m,$CH_2CH_2CH_2$,$CH_2CH_2$, $CH_2CH_2CH_2$)

NMR (300 MHz) $D_2O$ ST 848 δ8,2–8,1 (2H,2s,2CH ipoxantine); δ4.4 (2H,m,$CH_2$—N); δ4.3 (2H,m,$CH_2$—O); δ4.2-4(3H,m,$CH_2$—N,CHN); δ3,2 (2H,m,$CH_2$—N=C); δ3.0 (2H,m,CH2—COO); δ2.8-2.6 (2H,m,C$\underline{H}_2$—N$\underline{H}_2$); δ2-1.2 (16H,m,$CH_2CH_2CH_2$,C$\underline{H}_2$—$CH_2$,$CH_2$—$CH_2$—$CH_2$)

EXAMPLE 8

Preparation of N-5-(ipoxantin-9-yl) pentyloxycarbonyl L-alpha-aspartyl L-lysyl L-arginine (ST 872)

5.54 g (0.064 moles) of $NaHCO_3$ were dissolved in 100 mL $H_2O$; the solution was placed in an ice-bath and 6.71 g (0.040 moles) of tripeptide (Asp-Lys(Z)-Arg).$2CH_3COOH$ were added to the solution. To the resulting mixture 3.52 g (0.011 moles) of 9-(5-chlorocarbonyloxypentyl) ipoxantine hydrochloride were added.

The resulting reaction mixture was kept under stirring overnight and, upon reaction termination, brought to dryness. The product thus obtained was purified in a silica gel column, eluting with AcOEt: MeOH 3:7.

6.0 g of an intermediate product were obtained that was catalytically hydrogenated with 10% Pd/C at the pressure of 3 atmospheres in a $H_2O$/MeOH/HCl (50 mL/50 mL/0.77 mL) mixture. After 12 hours, the catalyst was filtered off and the filtrate brought to dryness at 40° C.

The product thus obtained was dissolved in water and the solution was lyophilized. 2 g of the title compound as an adduct with 1 NaCl molecule and 1 HCl molecule were obtained.

Yield 33%

$[\alpha]_D = -12.3$ (c=1% $H_2O$)

KF=2.4%

EA corresponds to $C_{27}H_{44}Cl_2N_{11}NaO_9$

MP=218°–221° C.

TLC=$CHCl_3$—MeOH—IsoprOH—$H_2O$—$CH_3COOH$ (42-28-7-10.5-10.5)

$R_F = 1.33$

NMR (300 MHz) $D_2O$ δ8.2–8.1 (2H,2s,2CH (ipoxantine); δ4.4–4.3 (2H,m,$CH_2$N); δ4.3–4.2 (2H,m,$CH_2$—O); δ4.2 (2H,m,$CH_2$—N); δ4.1 (1H,m,CH—N); δ3.2 (2H,m,$CH_2$—N=C); δ3.0 (2H,m,$CH_2$COO); δ2,9–2,6 (2H,m,C$\underline{H}_2$—$NH_2$); δ2-1.2 (16H,m,$CH_2$—$CH_2$, $CH_2$—C$\underline{H}_2$,$CH_2$—$CH_2$—$CH_2$)

EXAMPLE 9

Preparation of N-5-(ipoxantin-9-yl) pentyloxycarbonyl L-valyl L-alpha-aspartyl L-lysyl L-arginine (ST 873)

4.62 g (0.055 moles) of $NaHCO_3$ were dissolved in 100 mL $H_2O$. To this solution, cooled to 0° C., 6.87 g (0.01 moles) of (Val-Asp-Lys(Z)-Arg).HCl tetrapeptide (SEQ ID NO: 2) were added. Following complete dissolution, 3.52 g (0.011 moles) of 9-(5-chlorocarbonyloxypentyl) ipoxantine hydrochloride were added and the resulting mixture was kept under stirring at room temperature overnight.

The reaction mixture was then brought to dryness and the product thus obtained was purified in a silica gel column, eluting with MeOH.

4.3 g of an intermediate product were obtained that were dissolved in 50 mL of a MeOH/$H_2O$ (9:1) solution to which 0.49 cc conc.HCl were added.

The mixture was catalytically hydrogenated with 10% Pd/C at 3 atmospheres of hydrogen overnight. Upon reaction termination, the catalyst was filtered off and the filtrate brought to dryness. The residue was taken up with water and the resulting solution was lyophilized. 2.2 g of the title compound as an adduct with 2 NaCl molecules were obtained.

Yield 35%
$[\alpha]_D = -27.5$ (c=1% H$_2$O)
KF=3.8%
EA corresponds to C$_{32}$H$_{52}$Cl$_2$N$_{12}$Na$_2$O$_{10}$
MP=210°-212° C.
TLC=CHCl$_3$—MeOH—IsoprOH—H$_2$O—CH$_3$COOH (42-28-7-10.5-10.5)
R$_F$=1.85
NMR (300 MHz) δ8.2 (2H,2s,2CH ipoxantine); δ4.7 (2H,m,2CH—N); δ4.4–4.2 (2H,m,CH$_2$—O); δ4.2–4.1 (2H,m,CH$_2$—N); δ3.8 (1H,d,CH—N); δ3,2 (2H,m,CH$_2$—NH—C); δ3(2H,m,CH$_2$—COO); δ2,8–2,5(2H—m—CH$_2$NH$_2$);

2,0–1,2(17H, m, CH$_2$—CH$_2$—CH$_2$, CH$_2$—CH$_2$,

CH$_2$—CH$_2$—CH$_2$, CH$\diagdown^{\diagup}$ );

δ1.0 (6H,d,2CH$_3$)

EXAMPLE 10

Preparation of N-5-(ipoxantin-9-yl) pentyloxycarbonyl L-arginyl L-lysyl L-alpha-aspartyl L-valyl L-tyrosine (ST 897)

2.78 g (0.012 moles) of NaHCO$_3$ were dissolved in 100 mL H$_2$O. To this solution, cooled to 0° C., 3.35 g (0.0041 moles) of Arg-Lys(Z)-Asp-Val-Tyr pentapeptide (SEQ ID NO: 4) were added. To the resulting mixture 2.6 g (0.008 moles) of 9-(5-chlorocarbonyloxypentyl) ipoxantine hydrochloride were added portionwise. The reaction mixture was kept under stirring at room temperature overnight and, upon reaction termination, was then brought to dryness. The residue was purified by flash chromatography using CH$_2$Cl$_2$—MeOH (8:2–1:1) as eluant.

2.2 g of product were obtained which were dissolved in 50 mL of a MeOH/H$_2$O (9:1) mixture. To this solution 4 mmoles of conc.HCl were added. The resulting mixture was catalytically hydrogenated with 10% Pd/C at 3 atmospheres of hydrogen overnight. After 12 hours, the catalyst was filtered off and the filtrate brought to dryness. The residue was taken up with water and the solution lyophilized. 2 g of the title compound as an adduct with 2 NaCl molecules and 2 HCl molecules were obtained.

Yield 33%
$[\alpha]_D = -29.5$ (c=1% H$_2$O)
MP=164°-171° C. (softens)
200° C. (decarboxylates)
EA corresponds to C$_{41}$H$_{63}$Cl$_4$N$_{13}$Na$_2$O$_{12}$
HPLC: columnμ Bondapack C$_{18}$; mobile phase=KH$_2$PO$_4$ 0.05M-CH$_3$CN (85:15); U.V. detector: λ=205 nm; flow rate; 1 mL/min; Retention time: 36.9 minutes
NMR '300 MHz) D$_2$O; δ8.2–8.1 (2H,2s, s,2CH ipoxantine); δ7.1–6.7 (4H,dd,arom); δ4.6 (5H,m,5CH—N); δ4.3–4.2 (2H,m,CH$_2$—O); δ4.1–3.9 (2H,m,CH$_2$—N); δ3.2 (2H,m,CH$_2$—NH—C); δ3.0 (2H,m,CH$_2$—COO); δ3–2.7 (2H—m—CH$_2$—NH$_2$);

δ 2.0–1.1(19H, m, CH$_2$—Ar, CH$_2$—CH$_2$—CH$_2$,

CH$_2$—CH$_2$—CH$_2$, CH$\diagdown^{\diagup}$, CH$_2$CH$_2$);

δ0.8 (6H,m,2CH$_3$)
TLC: CHCl$_3$—MeOH—IsoprOH—H$_2$O—CH$_3$COOH (42-28-7-10,5-10,5) RF=0,4

The activity of the compounds of the present invention was assessed via several immuno-pharmacological tests. Some of these tests, wherein N-5-(ipoxantin-9-yl) pentyloxycarbonylarginine (hereinbelow briefly designated "ST 789") is used as reference compound, are illustrated below.

Test 1 Assessment of the effect of ST 657 and ST 789 on the primary antibody production (Jerne test) in the spleen of SRBC (Sheep Red Blood Cells) immunized mice.

Male B$_6$D$_2$F$_1$ mice (Charles River, Italy) aged 7–8 weeks (6 animals per group) were used. In this test, the animals were examined separately.

The compounds were administered i.p. at the doses of 2.5 and 25 mg/kg (single administration) the same day of immunization (Table 1) or, at the dose of 2.5 mg/kg/day (repeated administrations), at days −2, 0 and +2 (immunization at day 0) (Table 2).

The experimental procedure has been described by Jerne, N.K. et al, Transpl. Rev., 18, 130 (1974). In particular, the animals were immunized by i.p. administrations of a SRBC suspension (1×10$^7$ cells/mouse in 0.2 mL of sterile saline).

5 days following treatment, the spleens were aseptically excised from the sacrificed animals.

The concentration of the splenocytes obtained from the spleen was adjusted to 1×10$^7$ cells/mL. Aliquots of 0.1 mL of suspension were mixed with warm agar-Hank's (2 mL) and 10% SRBC in PBS buffer (0.2 mL), seeded in Petri dishes and incubated at 37° C. for 60 minutes (samples tested in triplicates). Following addition of complement (2 mL of guinea pig serum diluted 1:10 in Tris buffer), Petri dishes were further incubated at 37° C. for 30 minutes. In the presence of complement, the antibody-secreting cells of splenocytes extracted from the spleens of SRBC-immunized mice cause a hemolytic reaction. This reaction brings about the formation of lytic plaques in the samples.

The results obtained are expressed as follows:
(a) number of plaque-forming cells (PFC) out of 10$^6$ cells;
(b) number of plaque-forming cells in the whole spleen.

The data obtained are processed with Dunnett's test (Biostatistics in Pharmacology, vol. II, Pergamon Press) to assess the statistical significance of differences recorded between groups of treated and control animals.

As shown in the following tables, ST 657 is more active than ST 789 in increasing PFC number with respect to control.

TABLE 1

Assessment of the number of plaque-forming cells (PFC) in the spleen of SRBC-immunized mice treated with ST 657 on the day of immunization.

| Treatment | PFC/10$^6$ cells (x and ranges of variation) | PFC/spleen (x and ranges of variation) |
|---|---|---|
| Control | 295 (258–337) | 47683 (42104–54001) |
| ST 789 25 mg/kg | 339 (318–360) | 58137 (54505–62010) |

TABLE 1-continued

Assessment of the number of plaque-forming cells (PFC) in the spleen of SRBC-immunized mice treated with ST 657 on the day of immunization.

| Treatment | PFC/$10^6$ cells (x and ranges of variation) | PFC/spleen (x and ranges of variation) |
|---|---|---|
| ST 657 25 mg/kg | 422 (403–443)▲ | 61276 (54294–63323) |
| ST 657 2,5 mg/kg | 393 (368–420) | 62356 (59939–64871)▲ |

Dunnett's test = ▲ $p \leq 0.05$

TABLE 2

Assessment of the number of plaque-forming cells (PFC) in the spleen of SRBC-immunized mice treated with ST 657 at days −2, 0, +2 (immunization at day 0).

| Treatment | PFC/$10^6$ cells (x and ranges of variation) | PFC/spleen (x and ranges of variation) |
|---|---|---|
| Control | 284 (266–302) | 51377 (47191–55934) |
| ST 657 2,5 mg/kg | 416 (372–465)▲ | 67195 (59781–75529) |

Dunnett's test = ▲ $p \leq 0.05$

Test 2 Assessment of the protective effect induced by ST 657, ST 733, ST 754 and ST 789 on immunodepressed mice experimentally infected.

Male CD1 mice (Charles River, Italy) of different ages were used: mice aged 6 and 12 weeks infected with Klebsiella and mice aged 7 weeks infected with Salmonella (10 mice per group).

Systemic infection in mice was induced via i.p. inoculum of either a pathogenic strain of Klebsiella (K. pneumoniae) or a pathogenic strain of Salmonella (S. typhimurium), which were able to provoke death of the animals within 5 and 20 days, respectively, following the challenge.

Infective doses prepared from overnight broth cultures corresponding to $1.5 \times 10^5$ and $3.5 \times 10^5$ live cells of K. pneumoniae, and $1 \times 10^3$ live cells of S. typhimurium were suspended in 0.2 mL of 5% gastric mucine and then injected.

The immunosuppressor (cyclophosphamide) was administered i.p. in 0.2 mL of sterile saline, 100 mg/kg, 5 days before the infective challenge.

The compounds were administered i.p., 0.25 and 25 mg/kg/day, from day −5 to day −1 (challenge at day 0).

The results obtained are expressed as % mortality and statistically processed with the Fisher's exact test (Biostatistics in Pharmacology, vol. II, Pergamon Press).

As shown in the following tables, ST 657 exhibits a protective effect more potent than ST 789.

Compounds ST 733 and ST 754 (relevant data not shown in the tables) were administered i.p. (25 mg/kg/day) from day −5 (cyclophosphamide administration day) to day −1 (challenge at day 0) and tested utilizing Klebsiella oxytoca as infectious agent. The group of immunodepressed infected animals treated with the compounds exhibited no mortality at all versus 44% mortality in the control group (immunodepressed, infected, untreated animals).

TABLE 1

Protective effect of ST 657 administered i.p. from day −5 to day −1 (challenge at day 0) in immunodepressed mice experimentally infected with K. pneumoniae.

| Treatment | K. pneumoniae ($1.5 \times 10^5$ cells)* % Mortality | K. pneumoniae ($3.5 \times 10^5$ cells)** % Mortality |
|---|---|---|
| Control[a] | 0 | 10 |
| Immunodepressed control[b] | 90 | 90 |
| ST 789 0.25 mg/kg[c]/day | 50 | 50 |
| ST 789 25 mg/kg[c]/day | 40 $p < 0.05$ | 60 |
| ST 657 0.25 mg/kg[d]/day | 50 | 33*** $p < 0.01$ |
| ST 657 25 mg/kg[d]/day | 20 $p < 0.01$ | 60 |

[a] = infected animals
[b] = infected animals following immunodepression
[c] = immunodepressed animals, treated with ST 789 (at the dose indicated) and then infected
[d] = immunodepressed animals, treated with ST 657 (at the dose indicated) and then infected
*challenge in animals aged 6 weeks
**challenge in animals aged 12 weeks
***group consisting of 9 animals
Statistical calculations performed with Fisher's exact test.

TABLE 2

Protective effect of ST 657 administered i.p. from day −5 to day −1 (challenge at day 0) in immunodepressed mice experimentally infected with Salmonella typhimurium ($1 \times 10^3$ cells).

| Treatment | % Mortality |
|---|---|
| Control[a] | 10 |
| Immunodepressed control[b] | 60 |
| ST 789 0.25 mg/kg[c]/day | 10 $p < 0.05$ |
| ST 789 25 mg/kg[c]/day | 20 n.s. |
| ST 657 0.25 mg/kg[d]/day | 0 $p < 0.01$ |
| ST 657 25 mg/kg[d]/day | 0 $p < 0.01$ |

[a] = infected animals
[b] = infected animals following immunodepression
[c] = immunodepressed animals, treated with ST 789 (at the dose indicated) and then infected
[d] = immunodepressed animals, treated with ST 657 (at the dose indicated) and then infected
Statistical calculations performed with Fisher's exact test.

Test 3 Assessment of the "in vitro" and "in vitro-ex vivo" effect of ST 657 and ST 789 on the chemotactic activity of rat granulocytes.

Male Fisher-344 rats aged about 3 months were used (6–8 animals for each experimental group).

The compounds were tested "in vitro", 10 mcg/mL, and "in vitro-ex vivo" following administration of 25 mg/kg/day from day −5 to day −1 (taking of blood sample at day 0).

The experimental procedure is described by Cates, L. K. et al (1987), Modified Boyden chamber method of measuring polymorphonuclear leukocyte chemotaxis, Leukocyte Chemotaxis, Raven Press, N.Y. 67.

Blood samples were collected from animals sacrificed by decapitation. Following passage through heparinized gauze, blood was diluted (1:1) with dextran (1.5% in saline) and allowed to sediment for 90 minutes.

The concentration of the granulocytes, collected from blood via known techniques, was adjusted to $2 \times 10^6$ cells/mL in Hank's medium. They were then seeded on 3 μMillipore filters which were placed in migration chambers.

These chambers were prepared using Hank's medium to evaluate the spontaneous migration, and casein (2 mL of solution, at the concentration 5 mg/mL) to evaluate the induced migration.

In performing the "in vitro" test, granulocytes of untreated animals were used, to which the compounds had been added before seeding thereof on the Millipore filters preparation of migration chambers.

Following incubation of the samples at 37° C. and 5% $CO_2$ for 60 minutes, the filters were stained and mounted on microscope slides.

Microscopic examination of samples versus control allows the distance (in μm) run by the two most forward granulocytes in the framed field to be determined. Granulocyte migration is determined by calculating the mean value of 10 readings performed as a whole on two filters per sample.

As shown in the following table, ST 657 is effective in enhancing the chemotactic activity of rat granulocytes versus the control. ST 789 is totally inactive.

The results obtained were statistically processed with Student's "t" test (Biostatistics in Pharmacology, loc, cit.).

TABLE 1

Effect of ST 657 on the "in vitro and "in vitro-ex vivo" chemotactic activity of rat granulocytes.

| Treatment | "in vitro" chemotaxis (μ ± S.E.) | Treatment[a] | "in vitro-ex vivo" chemotaxis (μ ± S.E.) |
|---|---|---|---|
| Control | 46.2 ± 2.36 | Control | 80.6 ± 3.14 |
| ST 789 10 mcg/mL | 38.8 ± 4.47 | ST 789 | 79.8 ± 1.53 |
| ST 657 10 mcg/mL | 54.8 ± 3.05▲ | ST 657 | 89.3 ± 1.95▲ |

[a]= compounds administered i.p. at the dose of 25 mg/kg/day from day −5 to day −1
▲Student's "t" test = p ≤ 0.05

Test 4 Assessement of the protective effect of ST 657 and ST 789 in tumor-bearing mice.

Male DBA/2 mice and male CD1 mice (Charles River), both aged 6 weeks, were used.

DBA/2 mice were inoculated i.p. with $1 \times 10^5$ Leukemia L 1210 cells (ATCC-American Type Culture Collection-Cell Lines & Hybridomas, 5th Ed., 1985) in 0.1 mL of Hank's medium.

CD1 mice were inoculated i.p. with $1 \times 10^3$ Sarcoma S 180 cells (ATCC, loc. cit.) in 0.1 mL of Hank's medium.

The compounds were adminstered i.p. in sterile saline (0.25 mg/kg/day) from day +1 to day +10 (tumor transplantation at day 0).

Also the body weight of the animals was monitored, from day 0 to day +16 for the L 1210 leukemia-bearing mice, and from day 0 to day +21 for the S 180 sarcoma-bearing mice.

Monitoring of body weight was conducted in order to evaluate the evolution of the neoplastic process. Compounds activity was assessed as Mean Survival Time (MST).

As shown in the following tables, ST 657 exhibits a higher MST and/or a better protection than ST 789.

TABLE 1

Protective effect of ST 657[a] in S 180 Sarcoma-bearing mice

| Treatment | Dead/total | MST[b] |
|---|---|---|
| Control | 8/10 | 20.5 (18.0−≧29.8) |
| ST 789 (0.25 mg/kg) | 8/9 | 22.0 (20.5−≧25.5) |
| ST 657 (0.25 mg/kg) | 5/9 | 26.0 (20.5−≧47.0) |

[a]= i.p. administrations from day +1 to day +10.
[b]= mean survival time calculated by the median and the first interquartile range.
Control = untreated sarcoma-bearing mice.

TABLE 2

Weight control ($\bar{x}$ ± S.E.) of S 180 Sarcoma-bearing mice treated i.p. with ST 657 from day +1 to day +10. Next to the weights, the number of surviving animals at the indicated day is reported.

| Day | Blanks (5)[b] | Controls (10)[b] | ST 789[a] (9)[b] | ST 657[a] (9)[b] |
|---|---|---|---|---|
| 0 | 22.3 ± 0.4 | 22.1 ± 0.4 | 21.8 ± 0.5 | 22.2 ± 0.3 |
| 2 | 24.4 ± 0.4 | 22.3 ± 0.4 | 22.4 ± 0.5 | 22.0 ± 0.6 |
| 4 | 25.9 ± 0.4 | 25.4 ± 0.5 | 24.3 ± 0.6 | 23.9 ± 0.4 |
| 7 | 27.8 ± 0.5 | 28.0 ± 0.5 | 25.8 ± 0.7 | 26.1 ± 0.4 |
| 9 | 28.8 ± 0.6 | 31.1 ± 0.8 | 26.9 ± 0.8 | 27.3 ± 0.5 |
| 11 | 30.0 ± 0.6 | 33.4 ± 1.1 | 29.2 ± 1.2 | 28.6 ± 0.6 |
| 14 | 31.3 ± 0.6 | 36.0 ± 1.3 | 33.1 ± 2.0 | 31.2 ± 1.0 |
| 16 | 31.1 ± 0.6 | 37.6 ± 1.9[9] | 34.0 ± 2.0 | 31.4 ± 1.1 |
| 21 | 32.1 ± 0.5 | 38.2 ± 2.8[5*] | 32.8 ± 2.2[5*] | 32.9 ± 1.0[6*] |

[a]0.25 mg/kg/day
[b]number of animals in the group.
*An animal of the control group died on day +21, another one on day +22 and a third one on day +24. Two animals survived. Of the 5 animals of the ST 789 group, an animal died on day +22, a second one on day +23, a third one on day +25 and a fourth one on day +26. One animal survived. Of the 6 animals of the ST 657 group, an animal died on day +25 and a second one on day +26. 4 animals survived.
Blanks = healthy animals
Controls = untreated tumor-bearing animals.

TABLE 3

Protective effect of ST 657[a] in L 1210 Leukemia-bearing mice

| Treatment | Dead/total | MST[b] |
|---|---|---|
| Control | 10/10 | 14.0 (14.0−15.3) |
| ST 789 (0.25 mg/kg) | 9/9 | 14.0 (14.0−15.0) |
| ST 657 (0.25 mg/kg) | 10/10 | 15.5 (13.0−17.0) |

[a]= i.p. administrations from day +1 to day +10.
[b]= mean survival time calculated by the median and the first interquartile range.
Control = untreated tumor-bearing mice.

TABLE 4

Weight control ($\bar{x}$ ± S.E.) of L 1210 Leukemia-bearing mice treated e.p. with ST 657 from day +1 to day +10. Next to the weights, the number of surviving animals at the indicated day is reported.

| Day | Blanks (10)[b] | Controls (10)[b] | ST 789[a] (9)[b] | ST 657[a] (10)[b] |
|---|---|---|---|---|
| 0 | 19.3 ± 0.4 | 18.8 ± 0.4 | 18.2 ± 0.3 | 18.2 ± 0.5 |
| 2 | 19.3 ± 0.4 | 19.2 ± 0.5 | 18.0 ± 0.4 | 18.2 ± 0.5 |
| 4 | 20.8 ± 0.4 | 19.9 ± 0.5 | 19.1 ± 0.3 | 18.8 ± 0.5 |
| 7 | 21.6 ± 0.4 | 21.2 ± 0.4 | 20.1 ± 0.4 | 20.1 ± 0.4 |
| 9 | 22.2 ± 0.4 | 22.4 ± 0.5 | 21.8 ± 0.4 | 21.7 ± 0.6 |
| 11 | 22.9 ± 0.4 | 24.7 ± 0.6 | 24.0 ± 0.4 | 23.9 ± 0.8 |
| 14 | 23.3 ± 0.5 | 26.4 ± 0.8[4] | 22.7 ± 0.9[3] | 23.1 ± 0.6[6] |
| 16 | 23.1 ± 0.5 | 26.1[1*] | 22.5[1*] | 22.4 ± 0.6[3*] |

[a]0.25 mg/kg/day
[b]number of animals in the group.
*The animal of the control group died on day +18. The animal of the ST 789 group died on day +17.Of the three animals ST 657 group, 2 of them died on day +17 and 1 on day +18.
Blanks = healthy animals
Controls = untreated tumor-bearing animals.

Test 5 Assessment of the "in vitro-ex vivo" effect of ST 733 and ST 789 on the mytogen (PHA)-induced splenocyte proliferation in mice.

Male $B_6D_2F_1$ mice (Charles River, Italy) aged 7–8 weeks (4 animals per group) were used.

PHA (phytohemagglutinine) active on T lymphocytes was used as mytogen. The mytogen was tested at three different concentrations (suboptimal, optimal, superoptimal): 0.5, 2 and 4 mcg/mL/well.

The compounds were administered i.p. 25 mg/kg/day from day −5 to day −1 (spleen excision at day 0).

The experimental procedure was conducted substantially as described by Kirchner et al, "Splenic suppressor macrophages induced in mice by injection of C. parvum", J. Immunol., 1975, 115:1212.

In particular, the cell suspensions obtained from the spleens of the animals of the same group were pooled and the cell concentration was adjusted to $5 \times 10^6$ cell/mL.

To volumes of 0.1 mL of each sample, equal volumes of the mytogen preparation were added so as to obtain the previously indicated final concentrations.

Each sample was prepared in triplicate in U-bottom microtiters. A control, to which 0.1 mL of medium was added instead of the mytogen, was also prepared. The control permits the extent of spontaneous proliferation in the absence of stimulation to be assessed.

The samples were incubated at 37° C. for 48 hours and then they were pulsed with 20 μL $^3$H-TdR (25 μCi/mL).

After 18 hours of further incubation, the cells were collected on filters and counted in a beta-counter to evaluate the incorporated radioactivity (in cpm).

The results for each sample are expressed by calculating the value of the area under the curve (AUC) obtained by plotting the values of the incorporated radioactivity (in cpm) versus the three concentrations of mytogen.

In addition to AUC, also the stimulation index (SI) is considered, that is defined as follows:

$$SI = \frac{AUC \text{ treated}}{AUC \text{ control}}$$

The compound ST 789 brings about a slight increase in the mytogen-induced proliferation versus the controls; on the other hand, ST 733 provokes a remarkable increase in the same parameter (S.I.=1.82) as shown in the following table.

of SRBC solution ($2 \times 10^9$ cells/mL) were injected in the left hind foot-pad of the mice. The contralateral foot-pad received an equal volume of PBS. 24 hours after the challenge injection, the animals were sacrificed by cervical dislocation. The legs were amputated and the differences in weight between the left leg (treated with the challenge injection) and the contralateral leg were evaluated.

The mean of weight differences in the legs of the animals of the same experimental group was determined; the differences in the mean values calculated for each experimental group were processed using Student's "t" test (Biostatistics in Pharmacology, loc cit.).

The experimental procedure which was used is described by Miller, T. E. et al, (1973), Immunopotentiation with BCG. Modulation of the response to sheep red blood cells. J. Cancer Inst., 51:1669.

The compound St 785 is able to remarkably reduce the response to the DTH test ($p \leq 0.01$) (see the following table).

TABLE 1

Effect of ST 785 and ST 789 on the response to the DTH reaction vs. SRBC in mice. Administration of the substances (25 mg/kg/day) by i.p. route from day −3 to day +3 respect to the immunization.

| Treatment | Mean difference in weight (mg ± S.E.) between treated and untreated foot-pads |
|---|---|
| Control | 38.1 ± 3.03 |
| ST 789 | 34.9 ± 0.76 |
| ST 785 | 22.4 ± 3.79 ▲ |

Student's "t" test: ▲ $p \leq 0.01$

Test 7 Assessment of the "in vitro-ex vivo" effect of ST 754, ST 785 and ST 789 on the mytogen (PHA, Con

TABLE 1

"In vitro-ex vivo" effect of ST 733 on mytogen (PHA)-induced proliferation of splenocytes from mice i.p. treated (25 mg/kg/day) from day −5 to day −1 (spleen excision at day 0).

| Treatment | Body weight (g) | Spleen weight (mg) | Thymus weight (mg) | Splenocytes No. ($\times 10^7$)[a] | PHA AUC[b] | PHA I.S.[c] |
|---|---|---|---|---|---|---|
| Control | 24.3 ± 0.6 | 84.6 ± 4.8 | 73.0 ± 1.1 | 14.6 | 88 (80–95) | — |
| ST 789 | 23.9 ± 0.1 | 87.0 ± 4.5 | 64.5 ± 4.6 | 10.0 | 114 (108–121) | 1.30 (1.12–1.51) |
| ST 733 | 23.4 ± 0.2 | 74.0 ± 4.0 | 75.0 ± 4.0 | 14.7 | 160 (138–182) | 1.82 (1.44–2.27) |

[a] = pooled samples
[b] = area under curve ($\times 10^{-3}$) with the range of variation in brackets
[c] = stimulation index with the range of variation in brackets Test 6 Assessment of the effect of ST 785 and ST 789 on the delayed type hypersensitivity test (DTH).

Male $B_6D_2F_1$ mice (Charles River, Italy) aged 6, 12 and 16 weeks (8 animals per group) were used.

The compounds were administered i.p., 25 mg/kg/day from day −3 to day +3 (immunization at day 0). Immunization was carried out by s.c. injection in the upper dorsal zone of the animals of 0.2 mL of SRBC ($5 \times 10^7$ cells/mL).

Four days following the sensitizing injection, the animals were administered the challenge injection to bring about the delayed hypersensibility reaction. 50 μL A)-induced murine thymocite proliferation.

The compounds were administered at the dose of 25 mg/kg/day from day −4 to day −1 (thymus excision at day 0). This test was conducted following the procedure described for test 5. ST 785 and ST 754 are more potent than ST 789 in enhancing the extent of induced proliferation.

In particular, ST 754 exhibits S.I.=1.25 (Con A-induced proliferation); ST 785 exhibits S.I.=1.26 (Con A-induced proliferation) and S.I.=1.58 (PHA-induced proliferation) (see the following table). The Stimulation Index (S.I.) is as defined in test 5.

TABLE 1

"In vitro-ex vivo" effect of ST 754, ST 785 and ST 789 on mytogen (PHA, Con A)-induced proliferation of thymocytes from mice i.p. treated (25 mg/kg/day) from day −4 to day −1 (test at day 0).

| Treatment | Body weight (g) | Thymus weight (mg) | Thymocytes No. ($\times 10^7$)[a] | PHA AUC[b] | PHA I.S.[c] | Con A AUC[b] ($\times 10^{-3}$) | Con A I.S.[c] |
|---|---|---|---|---|---|---|---|
| Control | 23.2 ± 0.4 | 78.0 ± 3.1 | 13.8 | 2788 (2359–3217) | — | 62 (56–69) | — |

TABLE 1-continued

"In vitro-ex vivo" effect of ST 754, ST 785 and ST 789 on mytogen (PHA, Con A)-induced proliferation of thymocytes from mice i.p. treated (25 mg/kg/day) from day −4 to day −1 (test at day 0).

| Treatment | Body weight (g) | Thymus weight (mg) | Thymocytes No. ($\times 10^7$)[a] | PHA AUC[b] | PHA I.S.[c] | Con A AUC[b] ($\times 10^{-3}$) | Con A I.S.[c] |
|---|---|---|---|---|---|---|---|
| ST 789 | 22.8 ± 0.5 | 74.2 ± 4.4 | 12.1 | 3924 (3044–4804) | 1.40 (0.94–2.03) | 68 (66–71) | 1.10 (0.96–1.49) |
| ST 754 | 22.9 ± 0.5 | 74.0 ± 3.4 | 15.4 | 3132 (2407–3856) | 1.12 (1.75–1.63) | 78 (72–84) | 1.25 (1.05–1.49) |
| ST 785 | 22.5 ± 0.4 | 73.0 ± 2.7 | 15.1 | 4421 (4090–4752) | 1.58 (1.27–2.01) | 79 (73–86) | 1.26 (1.06–1.52) |

[a] = pooled samples
[b] = area under curve with the range of variation in brackets
[c] = stimulation index with the range of variation in brackets Test 8 Assessment of the "in vitro-ex vivo" effect of ST 733, ST 754 and ST 789 on the mixed lymphocyte reaction (MLR).

Male DBA/2 mice (Charles River, Italy) aged 8 weeks were used as "stimulators" (4 animals per group); male inbred C57B1/6 mice (Charles River, Italy) were used as "responders" (4 animals per group).

The compounds were administered i.p. from day −5 to day −1 (thymus excision of "responders" at day 0) 25 mg/kg/day.

The experimental procedure that was used is described by Hudson, L. and Hay, F. C., Practical Immunology, Blackwell Scientific Publication 290 (1980).

The compounds ST 733 and ST 754 are more potent than ST 789 in enhancing stimulators splenocytes-induced proliferation of responder thymocytes induced by stimulator splenocytes (see the following table).

TABLE 1

Effect of ST 733, ST 754 and ST 789 on the mixed lymphocyte reaction (MLR).
Proliferation of responders (thymus of C57B1/6) induced by stimulators (spleen of DBA/2).
Administration of the substances (25 mg/kg/day) by i.p. route from day −5 to day −1
(thymus excision at day 0).

| Treatment | Body weight (g) | Spleen weight (mg) | Thymus weight (mg) | Thymocytes No. ($\times 10^7$)[a] | $^3$H-TdR Incorporation (cpm ± S.E.) Non stimulated responders | $^3$H-TdR Incorporation (cpm ± S.E.) Stimulated responders |
|---|---|---|---|---|---|---|
| Control | 23.5 ± 0.8 | 91.0 ± 1.6 | 62.5 ± 1.5 | 19.3 | 103.5 ±22.6 | 6657 ±556 |
| ST 789 | 22.1 ± 0.5 | 82.7 ± 3.2 | 63.0 ± 7.9 | 14.7 | 132.0 ±11.1 | 9256 ±272 |
| ST 733 | 21.8 ± 0.8 | 88.7 ± 13.6 | 61.5 ± 2.7 | 15.5 | 163.0 ±23.1 | 11187 ±524 |
| ST 754 | 22.3 ± 0.5 | 81.2 ± 3.3 | 57.5 ± 8.4 | 12.9 | 89.2 ±19.9 | 11011 ±518 |

[a] = pooled samples

We claim:
1. N-5-(ipoxantin-9-yl) pentyloxycarbonyl glycyl L-aspartate disodium salt.

2. N-5-(ipoxantin-9-yl) pentyloxycarbonyl L-alpha-aspartyl L-arginine sodium salt.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:1:

Arg  Lys  Asp  Val
   1

( 2 ) INFORMATION FOR SEQ ID NO:2:

( i ) SEQUENCE CHARACTERISTICS:
      ( A ) LENGTH: 4 amino acids
      ( B ) TYPE: amino acid
      ( D ) TOPOLOGY: linear -continued (ii) MOLECULE TYPE: peptide (xi) SEQUENCE DESCRIPTION: SEQ ID NO:2:

Val Asp Lys Arg
1

(2) INFORMATION FOR SEQ ID NO:3:

(i) SEQUENCE CHARACTERISTICS:
 (A) LENGTH: 4 amino acids
 (B) TYPE: amino acid
 (D) TOPOLOGY: linear (ii) MOLECULE TYPE: peptide (xi) SEQUENCE DESCRIPTION: SEQ ID NO:3:

Thr Val Leu His
1

(2) INFORMATION FOR SEQ ID NO:4:

(i) SEQUENCE CHARACTERISTICS:
 (A) LENGTH: 5 amino acids
 (B) TYPE: amino acid
 (D) TOPOLOGY: linear (ii) MOLECULE TYPE: peptide (xi) SEQUENCE DESCRIPTION: SEQ ID NO:4:

Arg Leu Asp Val Tyr
1               5